(12) United States Patent
Walzman (10) Patent No.: US 11,065,021 B2
(45) Date of Patent: *Jul. 20, 2021

(54) OSTEOTOMY DEVICE (71) Applicant: Daniel Ezra Walzman, Bergenfield, NJ (US)

(72) Inventor: Daniel Ezra Walzman, Bergenfield, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 16/602,133

(22) Filed: Aug. 12, 2019

(65) Prior Publication Data
US 2020/0107846 A1 Apr. 9, 2020

Related U.S. Application Data (63) Continuation-in-part of application No. 16/151,335, filed on Oct. 3, 2018.

(51) Int. Cl.
| | |
|---|---|
| A61B 1/015 | (2006.01) |
| A61B 1/01 | (2006.01) |
| A61B 1/06 | (2006.01) |
| A61B 17/24 | (2006.01) |
| A61B 1/005 | (2006.01) |
| A61B 1/00 | (2006.01) |
| A61B 18/14 | (2006.01) |
| A61B 17/16 | (2006.01) |
| A61B 17/32 | (2006.01) |
| A61B 1/05 | (2006.01) |
| A61B 18/00 | (2006.01) |

(52) U.S. Cl.
CPC ............ *A61B 17/24* (2013.01); *A61B 1/0052* (2013.01); *A61B 1/00087* (2013.01); *A61B 1/00094* (2013.01); *A61B 1/00135* (2013.01); *A61B 1/01* (2013.01); *A61B 1/015* (2013.01); *A61B 1/051* (2013.01); *A61B 1/06* (2013.01); *A61B 17/1606* (2013.01); *A61B 17/1615* (2013.01); *A61B 17/320068* (2013.01); *A61B 18/1485* (2013.01); *A61B 2018/00327* (2013.01); *A61B 2018/00595* (2013.01); *A61B 2018/00982* (2013.01); *A61B 2217/005* (2013.01); *A61B 2217/007* (2013.01); *A61B 2218/002* (2013.01); *A61B 2218/007* (2013.01)

(58) Field of Classification Search
CPC ..... A61B 1/267; A61B 1/2673; A61B 1/2676; A61B 1/273; A61B 1/2733; A61B 1/317; A61B 1/00066; A61B 2017/320052; A61B 17/32; A61B 17/34; A61B 17/3415; A61B 17/3421; A61B 17/3423; A61B 2017/3445
USPC ................. 600/106–107, 115, 121–125, 105
See application file for complete search history.

(56) References Cited

U.S. PATENT DOCUMENTS

| | | | |
|---|---|---|---|
| 6,113,567 A | 9/2000 | Becker | |
| 6,234,958 B1* | 5/2001 | Snoke | A61B 1/00082 600/106 |
| 6,258,115 B1 | 7/2001 | Dubrul | |
| 6,398,795 B1* | 6/2002 | McAlister | A61B 17/068 227/179.1 |
| 6,527,704 B1* | 3/2003 | Chang | A61B 1/042 600/112 |
| 6,679,833 B2 | 1/2004 | Smith | |

(Continued)

*Primary Examiner* — Matthew J Kasztejna (57) ABSTRACT

The present disclosure teaches a novel medical device for osteotomy, capable of simultaneous aspiration, cauterization, image-acquisition, irrigation and tissue-protection, adapted for ear, nose and throat procedures, but available or other cavity surgeries.

21 Claims, 10 Drawing Sheets

(56) References Cited

U.S. PATENT DOCUMENTS

| | | |
|---|---|---|
| 6,749,601 B2 | 6/2004 | Chin |
| 7,131,969 B1 | 11/2006 | Hovda |
| 7,169,115 B2* | 1/2007 | Nobis ............ A61B 17/320016 |
| | | 600/564 |
| 7,186,252 B2* | 3/2007 | Nobis ............ A61B 17/320016 |
| | | 606/45 |
| 7,462,175 B2 | 12/2008 | Chang |
| 7,654,951 B2 | 2/2010 | Ishikawa |
| 7,662,089 B2 | 2/2010 | Okada |
| 7,927,272 B2* | 4/2011 | Bayer ................ A61B 1/00154 |
| | | 600/107 |
| 10,398,451 B2* | 9/2019 | Jackson, III ..... A61B 17/00234 |
| 2001/0002730 A1 | 10/2001 | Dubrul et al. |
| 2003/0020819 A1 | 11/2003 | Hovda et al. |
| 2004/0005899 A1 | 3/2004 | Marinello et al. |
| 2004/0006408 A1 | 4/2004 | Becker |
| 2005/0119524 A1* | 6/2005 | Sekine ........... A61B 17/320016 |
| | | 600/114 |
| 2005/0228260 A1* | 10/2005 | Burwell ................. A61N 5/062 |
| | | 600/408 |
| 2005/0272977 A1 | 12/2005 | Saadat |
| 2006/0063973 A1 | 3/2006 | Makower |
| 2006/0014931 A1 | 7/2006 | Becker |
| 2006/0189845 A1* | 8/2006 | Maahs ................. A61B 1/0008 |
| | | 600/146 |
| 2006/0264706 A1 | 11/2006 | Piskun |
| 2007/0137651 A1* | 6/2007 | Glassenberg ..... A61M 16/0486 |
| | | 128/207.15 |
| 2007/0244353 A1 | 10/2007 | Larsen |
| 2008/0051629 A1* | 2/2008 | Sugiyama .......... A61B 1/00193 |
| | | 600/114 |
| 2008/0071289 A1 | 3/2008 | Cooper |
| 2009/0216196 A1 | 8/2009 | Drontle et al. |
| 2009/0318798 A1* | 12/2009 | Singh ..................... A61B 1/012 |
| | | 600/424 |
| 2010/0211007 A1 | 8/2010 | Lesch |
| 2012/0172664 A1* | 7/2012 | Hayman ........... A61B 1/00045 |
| | | 600/109 |
| 2015/0141755 A1 | 5/2015 | Tesar |
| 2017/0360288 A1 | 12/2017 | Kim |

* cited by examiner

OSTEOTOMY DEVICE

CROSS-REFERENCES

This is a continuation-in-part application, claiming the benefit of priority to utility application Ser. No. 16/151,335, filed Oct. 3, 2018 (3 Oct. 2018).

BACKGROUND OF THE INVENTION

Field of the Invention

The described invention relates generally to medical devices, systems and methods used for surgery to cut, excise or otherwise shape bones, and more particularly to methods and devices for performing image guided interventional procedures to treat disorders of the paranasal sinuses, ears, nose or throat (ENT).

Prior Art

Osteotomy devices are numerous. They include devices for cauterizing, irrigating, aspirating, image-collection, and cutting, among others. These devices are generally stand-alone, and normally can only be used in pairs, occasionally threes. The imaging is of two types: the first involves external sensors with tagged instruments; the second involves image-collection, either prior to the surgery or mounted on an insertion device.

Image-guided surgical techniques and devices were developed for neurosurgery and have now been adapted for use in certain ear, nose and throat surgeries, including sinus surgeries. See, Kingdom T. T., Orlandi R. R., Image-Guided Surgery of the Sinuses: Current Technology and Applications, Otolaryngol. Clin. North Am. 37(2):381-400 (April 2004). Generally, image-guided surgery involves getting images prior to surgery and then using said images to help the surgeon to execute.

U.S. Patent Application Publication No. 20090216196 to Drontle et al. discloses an apparatus and method for accessing a sinus cavity. Drontle does not disclose a unitary, single lumen or side-slit feature as does the current invention, and teaches no built-in camera(s).

U.S. Pat. No. 6,527,704 to Chang et al. discloses an endoscopic camera system integrated with a trocar sleeve, having a side groove that channels devices parallel to the catheter. The present invention discloses a different structure, a side-slit which channels devices perpendicular to the body of the device U.S. Patent Application Publication No. 2015/0141755 to Tesar discloses surgical visualization systems Tesar discloses a plurality of cameras, but does not disclose the placement of at least two cameras in specific positions disclosed by the present invention.

While Image guided surgery typically employs electro-magnetic sensors/tracking systems, radiofrequency electro-magnetic sensors (e.g., electromagnetic coils) which are placed on the surgical instruments and on a localizer frame worn by the patient, they do not have built in irrigation and respiration systems.

The lack of built-in irrigation and aspiration systems is a shortcoming of the prior art. Image-guided surgery systems are used in sinus surgery and other ear, nose and throat procedures. More particularly, this shortcoming results in the requirement that the surgeon insert and remove separate irrigation and respiration systems causing delay in procedures. The presence of said separate systems causes sensors which have been mounted on proximal portions of the instruments (e.g., on the handpiece of the instrument) to be moved away from targeted surgery sites resulting in the reduction of the accuracy of sensor information.

There is a need to perform minimally invasive osteotomies, especially for ear, nose and throat sinus procedures, in a safe and less invasive manner, with smaller instruments, and direct visualization, to facilitate safe performance of these procedures with less need for general anesthesia and its associated risks, and less need for the costs associated with performance of these procedures in an OR (increased ability to perform in office setting, with lower costs). Also allows for protection of surrounding tissue during bone cuts. Currently only select balloon sinuplasty procedures are performed in this setting, but these are less effective at relieving symptoms, and have much higher rates of recurrent symptomatic sinus blockage/infections.

Additionally, a need exists to protect tissue near surgical target-sites. While some use of insertable shielding is described in the prior art, such shielding is difficult to position, tends to migrate out of position, and can cause irritation to tissue.

Therefore, a need exists for an osteotomy device or system which is faster, more efficient, and easier to use. A need exists to better protect tissue proximal a surgical target during osteotomic procedures. A need exists for an osteotomy device comprising one or more modalities used in non-operating theater settings.

SUMMARY OF THE INVENTION

The present invention combines numerous osteotomy devices as well as adding a device not described in the prior art. More particularly, the present invention combines a shielding device for tissue proximal to the targeted surgical site, a cutting device, a cauterization device, an aspiration device, an irrigation device, cameras/endoscopes, lighting into an optionally malleable and/or steerable device. This multifunctional device allows the simultaneous application of cutting, irrigating, aspirating, cauterizing, while feeding back live visual information to the user, while minimizing tissue injury.

According to one aspect, the described invention provides irrigation and aspiration systems which are integrated into devices that are useable to perform image-guided procedures as well as a variety of other image guided ear, nose and throat procedures.

Additionally, the present invention provides improvements and modifications to the prior art's image-guided surgery systems to facilitate the performance of image-guided surgery and other image ear, nose and throat procedures with mini al or less iatrogenic trauma to and/or alteration of anatomical structures that are not involved in the disorder being treated.

BRIEF DESCRIPTION OF THE DRAWINGS

FIG. 3 shows an ultrasound bone-cutter 561 cutting a portion 1999 of wall 999 positioned within slit 10. FIG. 3 further shows cauterization system 900 (either unipolar or bipolar using two edges of the slit, said bone-cutter drawn in dashed lines as not part of the claimed invention), both deployed through elongated cylinder 11 and outside slit 10, working adjacent with bone cutter 561 within wall 999. The simultaneous function is being monitored by camera 30 after being positioned by the user observing the target area via cameras 20 and 30, the cameras 20, 30 referenced above in para. [0016].

DETAILED DESCRIPTION OF THE INVENTION

Figure 1:
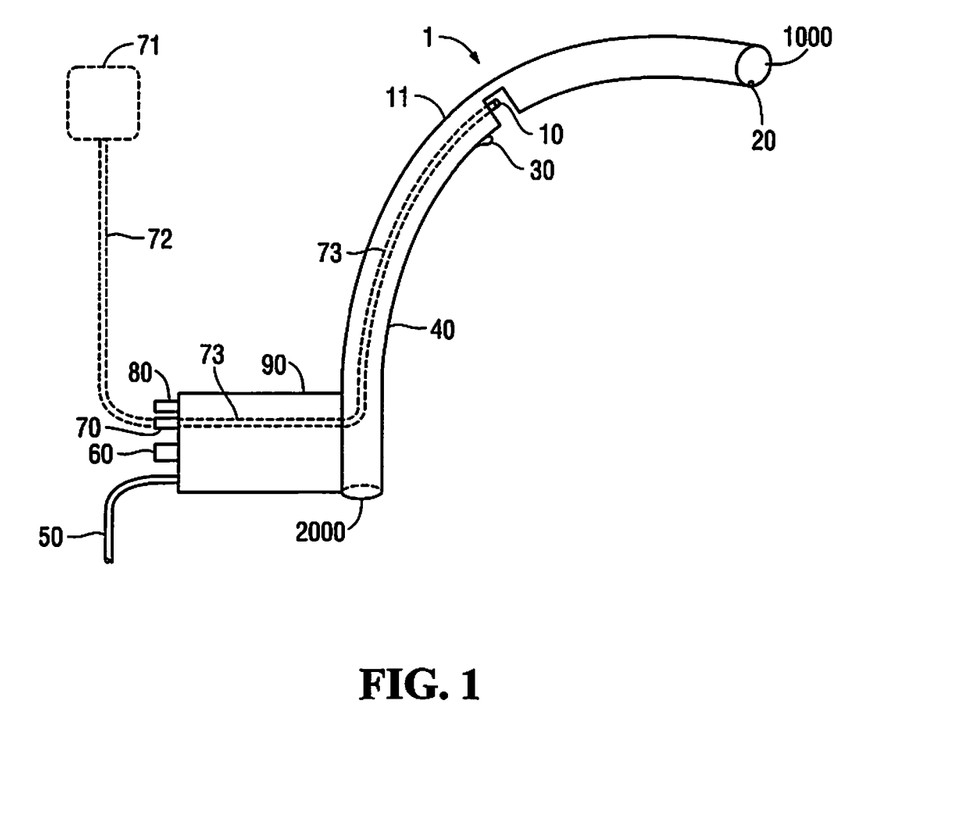
FIG. 1 illustrates an exemplary embodiment of the osteotomy device 1 of the disclosed invention, including nonoptional elements: distal hole 1000, proximal hole 2000, shielding element 11, a side-hole 10, side-camera 30 and end-camera 20, protective or hydrogel coating 40, and an optional square handle 90, optionally detachable, disposed outside the patient's body for control by the user. Additionally, disclosed is an illustration of a system composed of an aspiration controller 71, irrigation controller 81, external aspiration tube 72, external irrigation tube 82, internal aspiration tube 73, and internal irrigation tube 83. More particularly, aspiration tube 72 allows controller 71 to communicate through aspiration port 70 located in removable handle 90, to internal aspiration tube 73 which in turn terminates proximal to side slit 10 at the target site.

Now referring to FIG. 1, herein is described an osteotomy device 1 is composed of an elongate, straw-like cylinder 11 with proximal opening 2000 located outside the patient's body, and distal hole 1000 located inside the patient's body. Between proximal hole 2000 and distal hole 1000 is a side-slit 10 along the outside of cylinder element 11. Additionally, device 1 includes a handle 90, attached to cylinder 11. Handle 90 is optionally detachable when element 2 (illustrated in FIG. 2) is inserted through cylinder 11 via proximal hole 2000, and thereby rendering optional handle 90 redundant.

More particularly, cylinder 11 is composed of hard but flexible material suitable for protecting tissue proximal to a target surgical site. It is formed, optionally, of a biocompatible metal, plastic, or other suitable material, that is preferentially but optionally malleable. The cylinder including at least one side slit 10, wherein side slit 10 serves as a conduit to facilitate an osteotomy while the cylinder 11 helps to guide a cutting instrument in the proper orientation, and further serves to protect surrounding tissue from injury. Optional protective or hydrogel coating 40 assists insertion and further protects device and patient from irritation or injury.

Continuing with reference to FIG. 1, removable handle 90 includes optional cable for communicating with at least two cameras: end camera 20 and side camera 30 and optional lights (not shown); endoscopes (not shown) are delivered via proximal hole 2000. Additionally, handle 90 includes cable 50 for communicating and powering lights (not shown), cameras 20 and 30, and endoscopy scopes (not shown); optional cauterization-communication port 60, optional aspiration port 70, and optional irrigation port 80. Said handle 90 communicates with end camera 20 and side camera 30, as well as providing ports for aspiration via optional aspiration port 70 and irrigation via optional irrigation port 80. In a preferred embodiment, however, cable 50 is directed through handle 90; cauterization-communication port 60, aspiration port 70, and irrigation port 80 are all included.

Elongate cylinder 11 is disposed with at least two cameras/endoscope 20 and 30 along its length, with illumination. The camera or endoscope and lighting may be disposed at the distal tip and/or anywhere along the length of the exterior to facilitate direct, minimally invasive, and magnified visualization. The image may optionally appear in high-definition (HD) and/or three-dimensionally (3D). Out of side-hole 10 sonic, laser and other conventional cutting devices may be deployed simultaneously with irrigation and aspiration elements (not shown) but are introduced via optional ports 60, 70 and 80. More particularly, end camera 20 and side camera 30, as well as lights (not shown), endo-scope (not shown), and cutting devices (not shown) communicate through removable handle 90 through cable 50.

Figure 2:
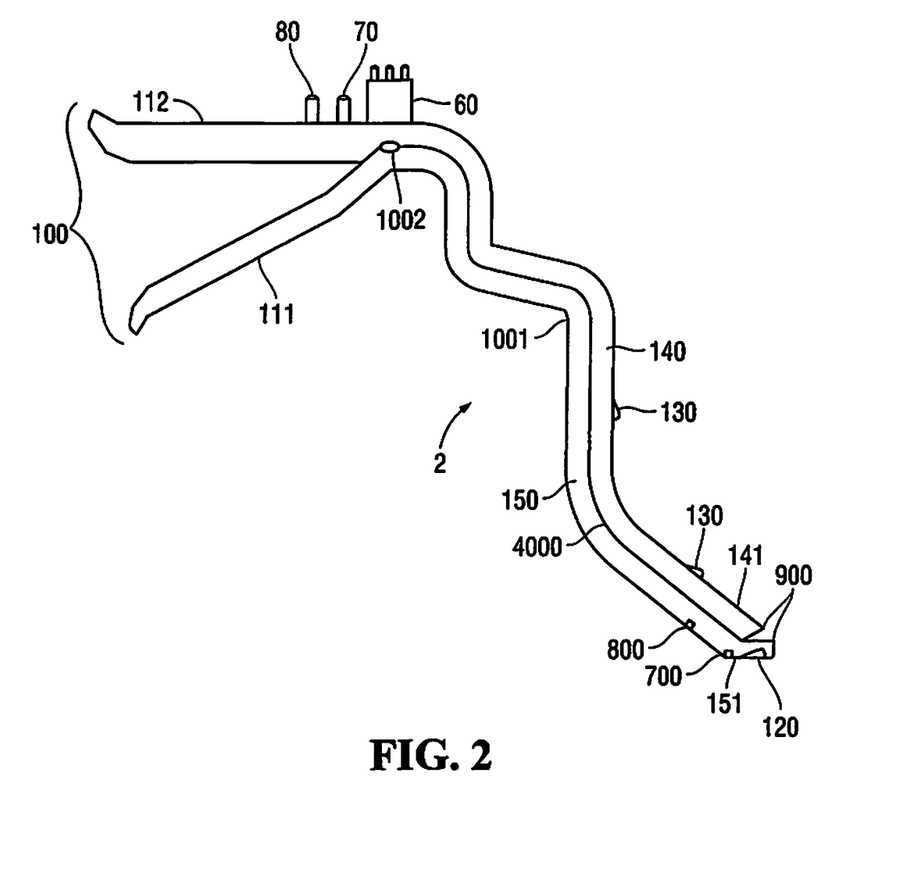
FIG. 2 illustrates device 2 including elements which may be used with osteotomy device 1, by insertion therethrough; said device 2 may be optionally connected to device 1. Alternatively, device 2 may be permanently attached to device 1 by inserting distal end of device 2 through proximal hole 2000 of device 1 form a third device.
Figure 3:
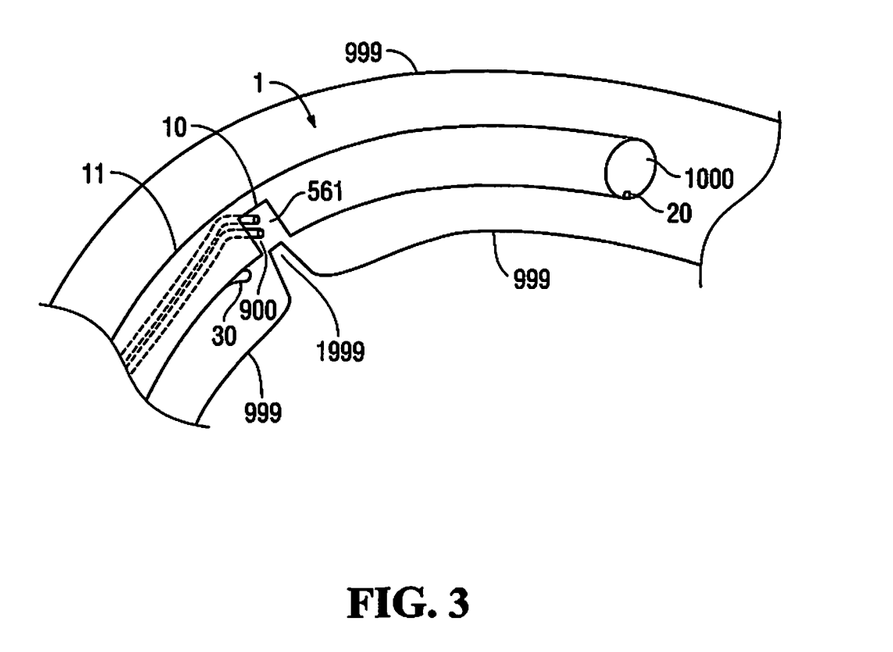
FIG. 3 shows a cutaway image of the device deployed within a vessel wall, further illustrating the use of slit 10 to shield the vessel during bone-cutting. More particularly.
Figure 4:
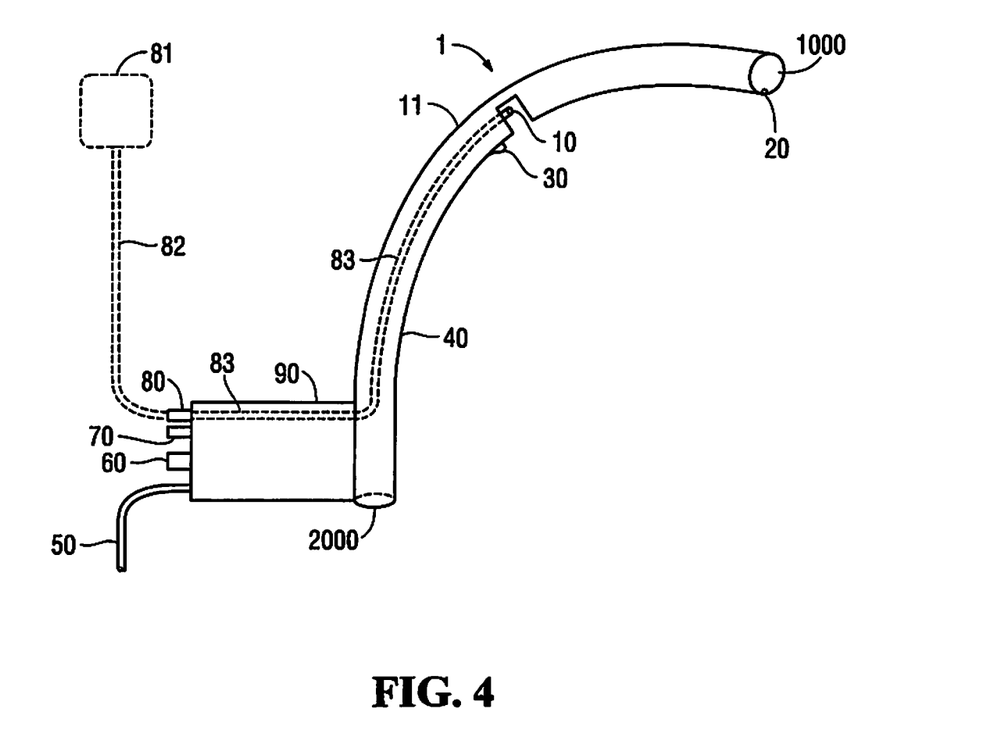
FIG. 4 illustrates an irrigation system (drawn in dashed lines as not part of the claimed invention, unless an irrigation lumen is embedded in a wall of the cylinder), composed of an irrigation controller 81, external irrigation tube 82 and internal irrigation tube 83. More particularly, irrigation tube 82 allows controller 81 to communicate through irrigation port 80 located in removable handle 90, to internal irrigation tube 83 which in turn terminates proximal to side slit 10 at the target site.
Figure 5:
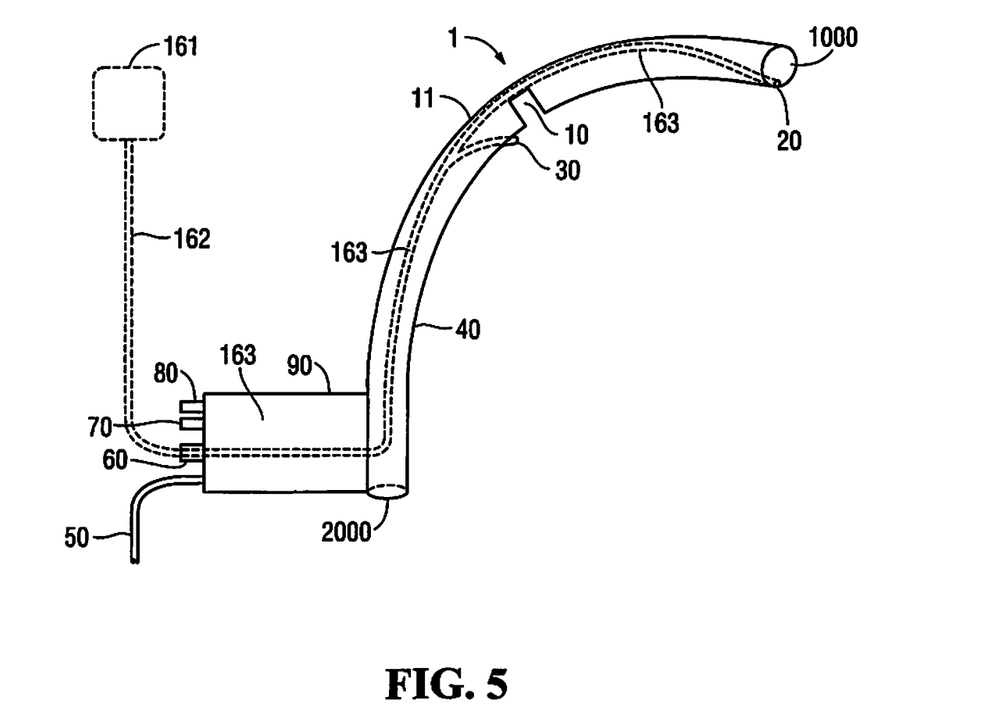
FIG. 5 illustrates an image-collection system (drawn in dashed lines as not part of the claimed invention), connecting to cameras 20 and 30, and composed of an image-collection controller 161, external image-collection circuit 162 and internal image-collection circuit 163. More particularly, image-collection circuit 162 allows controller 161 to communicate through port 60 located in removable handle 90, to internal image-collection circuit 163 which in turn connects to cameras 20 and 30.
Figure 6:
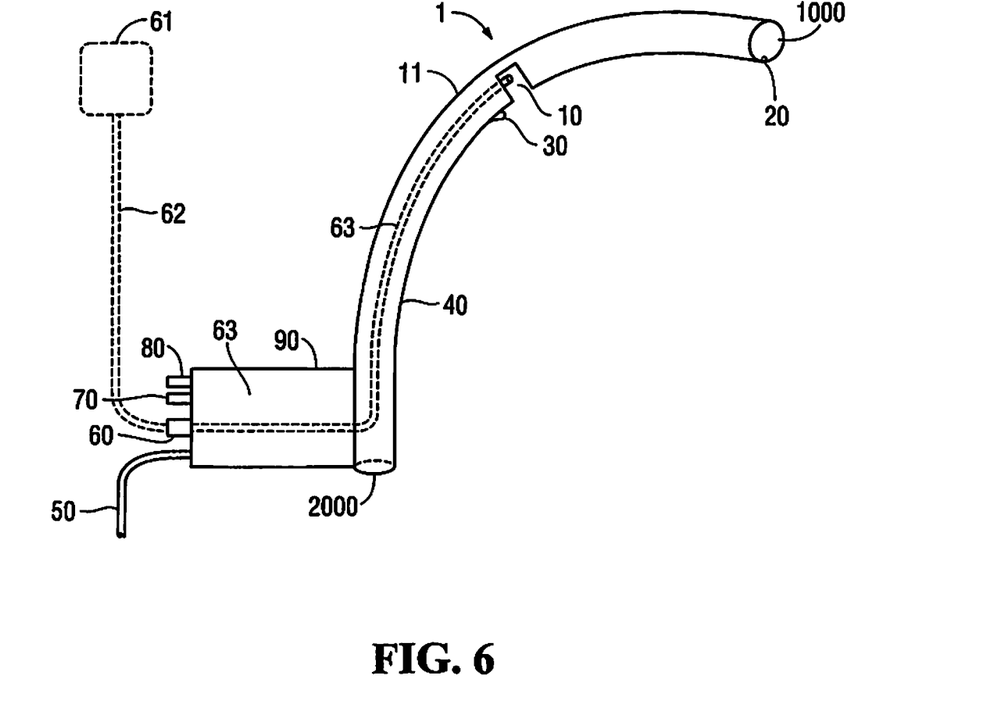
FIG. 6 illustrates when an embodiment of the present invention does not include insulated components of the wall of the cylinder ending at various points of the slit and/or the edges of the end hole 1000), then a cauterization-communication system (drawn in dashed lines as not part of the claimed invention) is provided composed of a cauterization-communication controller 61, external cauterization-communication circuit 62 and internal cauterization-communication circuit 63. More particularly, cauterization-communication circuit 62 allows controller 61 to communicate through cauterization-communication port 60 located in removable handle 90, to internal cauterization-communication circuit 63 which in turn terminates proximal to side slit 10 at the target site.
Figure 7:
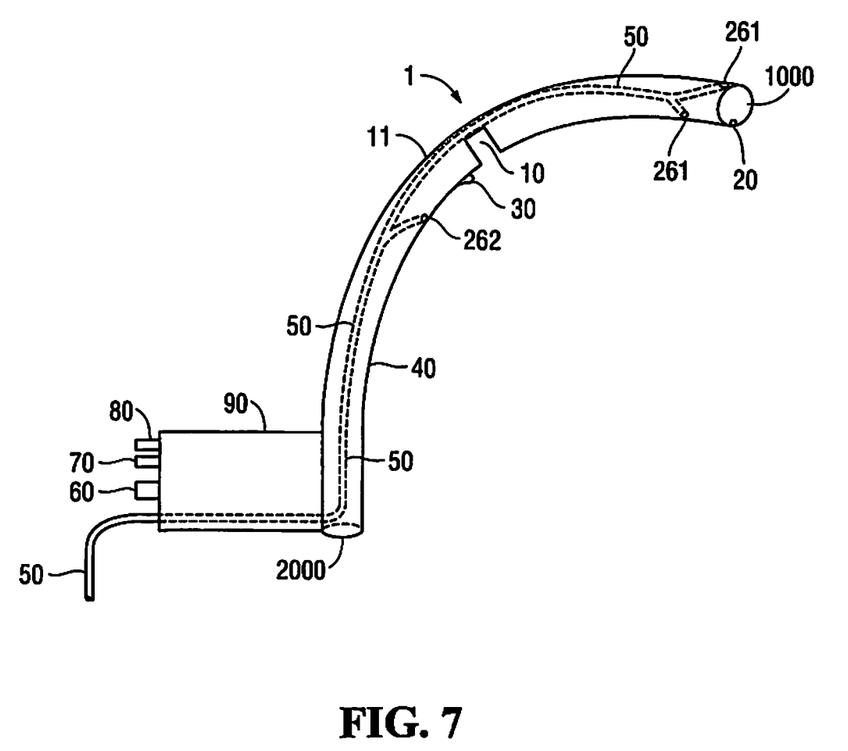
FIG. 7 illustrates cable 50 communicating through handle 90 to light-sources 261 and 262. In an alternate embodiment (not shown), the light sources and cameras are integrated, rather than implemented as a separate light exit (as shown in FIG. 7). In alternate embodiments, they may be separate components of the camera circuitry.
Figure 8:
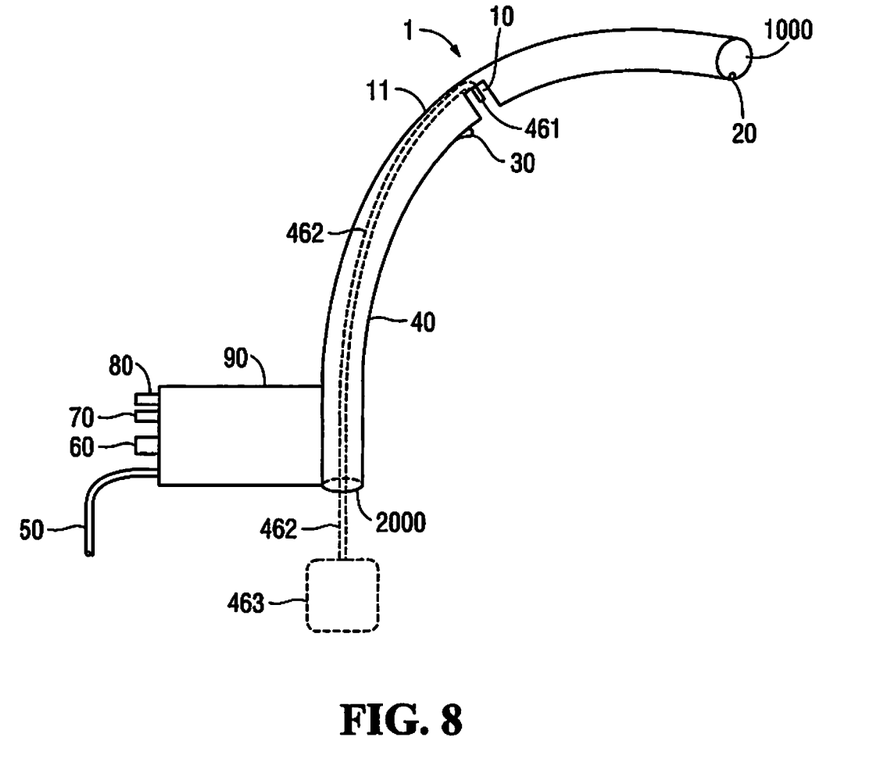
FIG. 8 illustrates a drill with a bone positioned in the slit; which drill remains in the slit in the preferred embodiment, such that an edge of bone/tissue is placed under visualization into the slit, then the drill is advanced in the protection of the cylinder and cut the bone contained within the slit, this embodiment being composed of a drill controller 463, communicating through proximal opening 2000 with drill circuit 462 to drill 461 disposed through side slit 10.
Figure 9:
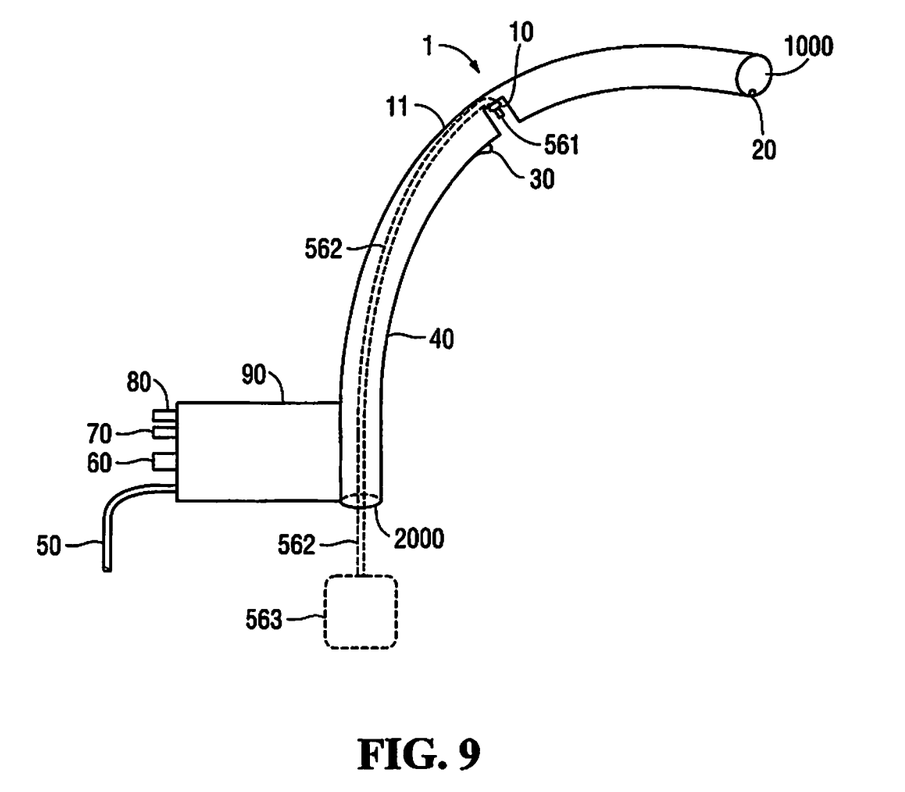
FIG. 9 illustrates an ultrasonic bone-cutter (referred to in FIG. 3, drawn in dashed lines as not part of the claimed invention), composed of an ultrasonic bone-cutter controller 563, communicating through proximal opening 2000 with ultrasonic bone-cutter circuit 562 to ultrasonic bone-cutter 561 disposed within the cylinder proximal to side slit 10.
Figure 10:
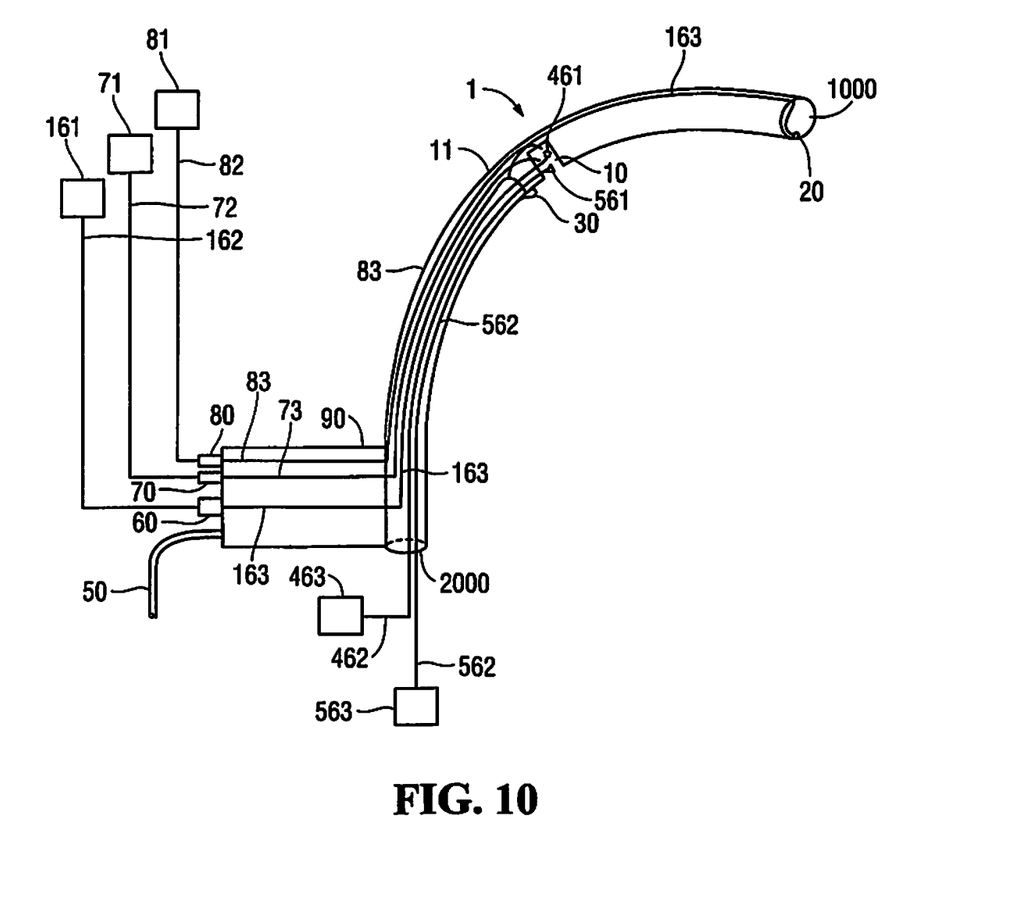
FIG. 10 depicts a combination of the various devices employed simultaneously.

Now referring to FIG. 2, device 2 has a proximal end handle 100, and a distal end camera 120, proximal to distal camera 120 are optional cauterization elements 900, aspiration hole 700, irrigation hole 800, and at least one optional side camera 130. Said distal end is integrated with device 1 from FIG. 1 by introducing distal camera end of device 2 into proximal hole 2000, and pushing device 2 through cylinder 11 until distal camera end is proximal to side-slit 10. Between handle 90 and distal camera end of device 2 are paired elements 1001 which is composed of upper element 140 and lower element 150 which slide against each other in response to the closing of handle 100 around joint 1002. More particularly, extending out from handle 100 are paired elements 1001. Handle 100 further comprises a combination element 1001 of upper sliding element 140 and lower sliding element 150 which, when activated, allows sliding elements 140 and 150 to slide against each other along interface 4000. When bottom handle element 111, and top handle element 112 are pinched together, lower element 150 retracts relative to upper element 140 toward handle 100, and the distal end 151 of element 150 moves closer to distal end 141 of element 140. When bottom element 111 is proximal to top element 112, distal end 141 of element 140 is proximal to distal end 151 of lower element 150. Together, distal ends of elements 141 and 151 form a cutting or clipping device. When 141 and 151 are opened and closed, device 2 is capable of dipping tissue or cutting bone. Furthermore, optional cauterization-communication port 60 allows external cameral systems to communicate with side-camera 130 and end-camera 120.

The above-described osteotomy device 1 is adaptable to a number of embodiments, desirable or necessary for differing procedures, as depicted in FIGS. 3-19.

In a preferred embodiment, the cylinder 11 is malleable, rendering cylinder 11 actively steerable. One or more of the optional embodiments of the osteotomic cylinder 11 may incorporate malleability and/or steerability.

In an optional embodiment, the cylinder 11 is incorporated with suction and/or irrigation functionality (not shown).

In another embodiment, the osteotomy cylinder 11 incorporates monopolar cautery and/or bipolar cautery 667. Said cautery capability may be disposed upon the tip or at the at least one slit of the cylinder as noted on FIG. 1 . . . .

In an optional embodiment, cylinder 11 incorporates a Kerrison bone punch. In this embodiment, the Kerrison punch may optionally be manual or powered.

In an optional embodiment, cylinder 11 incorporates a Kerrison rongeur (not shown). In this embodiment, the Kerrison rongeur may optionally be manual or powered.

In an optional embodiment, cylinder 11 incorporates a drill (not shown), optionally manual or powered. Cylinder 11 may be optimized to allow passage of a drill therethrough, for protected minimally invasive osteotomy.

In an optional embodiment, cylinder 11 incorporates an ultrasonic bone-cutter (not shown), optionally optimized to allow passage of a bone-cutter therethrough, for protected minimally invasive osteotomy.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials have been described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. An osteotomy system comprising: an aspiration system, an image-acquisition system, an irrigation system, an illumination system, a removable cutting instrument, and a tissue-protection catheter, wherein the aspiration system, the irrigation system and the cutting instrument are sheathed in the tissue-protection catheter, the tissue-protection catheter including: an elongate cylinder having a single protection lumen, a distal hole at a distal end portion, a proximal hole, at least one side-slit spaced from the distal end portion, and a handle, the side slit have a recessed region forming a tissue shielding area to shield the tissue within the slit and receive a tip of the cutting instrument, the slit open during insertion and cutting using the cutting instrument, and the cylinder having a substantially constant outer diameter along a length of the cylinder, the cylinder extending about a curve: wherein said handle comprises at least three ports, and wherein said handle is detachable from said elongate cylinder; and a first and second camera disposed along said cylinder, the second camera positioned proximal of the first camera and the first camera is distal of the side slit and positioned adjacent the distal hole of the cylinder, wherein the second camera extends from an external surface of the elongate cylinder and terminates proximal of a proximal wall of the recessed region, wherein the second camera is spaced from the first camera along the curve of the cylinder such that a length between the first and second cameras is defined along a non-linear path.

2. The osteotomy system of claim 1, wherein said cylinder is malleable.

3. The osteotomy system of claim 1, wherein the cutting instrument comprises a drill for cutting bone within said tissue shielding area.

4. The osteotomy system of claim 1, wherein the cutting instrument is an ultrasonic bone cutter.

5. The osteotomy system of claim 1, further comprising a cautery system.

6. The osteotomy system of claim 1, wherein said cylinder is steerable.

7. The osteotomy system of claim 1, wherein the irrigation system includes an irrigation tube extending through the elongate cylinder and terminating in the tissue shielding area.

8. The osteotomy system of claim 1, further comprising a first light source and a second light source proximal of the first light source.

9. The osteotomy system of claim 1, wherein the second camera extends outwardly from an external surface of the elongate cylinder for monitoring tissue adjacent the side slit and terminates proximal of the side slit.

10. The osteotomy system of claim 1, wherein the second camera extends from an external surface of the elongate cylinder and terminates proximal of the proximal wall of the recessed region.

11. The osteotomy system of claim 1, wherein the second camera is fixed with respect to the cylinder.

12. An osteotomy system configured for simultaneous operation of aspiration, image-acquisition, irrigation, illumination, and cutting, comprising:
    an elongate cylinder having a lumen and a substantially constant outer diameter along a length of the cylinder, the cylinder extending about a curve,
    a distal hole at a distal end portion,
    a proximal hole,
    a side slit between the proximal and distal hole, the side slit spaced from the distal end portion forming a recessed region to shield tissue during bone cutting, the recessed region having a proximal wall and a distal wall and the recessed region is open during insertion and cautery,
    wherein said proximal hole of said elongate cylinder is configured to allow a plurality of surgical instruments through the lumen and into the recessed region formed by the at least one side-slit, and
    a handle;
    wherein said handle comprises at least three ports, and
    at least a first and second camera disposed along said cylinder, the second camera positioned proximal of the first camera and the first camera is distal of the side slit and adjacent a distal hole of the cylinder wherein the second camera extends from an external surface of the elongate cylinder and terminates proximal of the proximal wall of the recessed region, and the second camera is spaced from the first camera along the curve of the cylinder such that a length between the first and second cameras is defined along a non-linear path;
    at least one cautery element terminating in the recessed region between the proximal and distal wall of the recessed region;
    a light source; and
    a cutting instrument, the cutting instrument terminating between the proximal wall and distal wall of the recessed region.

13. The osteotomy system of claim 12, wherein said cylinder is steerable.

14. The osteotomy system of claim 12, wherein the cutting instrument comprises a bone cutter terminating in the recessed region.

15. The osteotomy system of claim 14, further comprising an aspiration system having an aspiration tube terminating in the recessed region.

16. The osteotomy system of claim 12, wherein said cylinder is malleable.

17. The osteotomy system of claim 12, further comprising an aspiration system having an aspiration tube terminating in the recessed region.

18. The osteotomy system of claim 17, further comprising an irrigation system having an irrigation tube terminating in the recessed region.

19. The osteotomy system of claim 12, wherein the second camera is positioned proximal of the proximal wall of the recessed region.

20. The osteotomy system of claim 12, wherein an aspiration system and irrigation system terminate distal of the proximal wall and proximal of the distal wall and the second camera is spaced proximally from the distal wall.

21. The osteotomy system of claim 12, wherein the second camera is fixed with respect to the cylinder.

* * * * *